United States Patent [19]
Miyake et al.

[11] Patent Number: 6,048,712
[45] Date of Patent: Apr. 11, 2000

[54] PROCESS FOR PRODUCING α-MONOGLUCOSYL HESPERIDIN-RICH SUBSTANCE

[75] Inventors: Toshio Miyake, Okayama; Takashi Yumoto, Ichihara, both of Japan

[73] Assignees: Kabushiki Kaisha Hayashibara; Seibutsu Kagaku Kenkyujo, both of Japan

[21] Appl. No.: 09/194,190

[22] PCT Filed: Mar. 10, 1998

[86] PCT No.: PCT/JP98/00977

§ 371 Date: Nov. 23, 1998

§ 102(e) Date: Nov. 23, 1998

[87] PCT Pub. No.: WO98/42859

PCT Pub. Date: Oct. 1, 1998

[30] Foreign Application Priority Data

Mar. 24, 1997 [JP] Japan .................................. 9-069588

[51] Int. Cl.[7] .............................. C12P 19/60; C12P 19/44; C12P 19/20; C12P 19/14; C07G 3/00
[52] U.S. Cl. ................................ 435/75; 435/74; 435/78; 435/96; 435/99; 435/105; 536/4.1; 536/124
[58] Field of Search ................................ 435/74, 75, 78, 435/96, 99, 105; 536/4.1, 124

[56] References Cited

U.S. PATENT DOCUMENTS

| | | | |
|---|---|---|---|
| 3,583,894 | 6/1971 | Horowitz et al. | 195/31 |
| 4,332,825 | 6/1982 | Miyawaki et al. | 426/330.5 |
| 5,077,206 | 12/1991 | Cheetham et al. | 435/99 |
| 5,641,659 | 6/1997 | Meiwes et al. | 435/105 |
| 5,652,124 | 7/1997 | Hijiya et al. | 435/78 |

FOREIGN PATENT DOCUMENTS

| | | |
|---|---|---|
| 0402049 | 12/1990 | European Pat. Off. . |
| 3-07593 | 1/1991 | Japan . |
| 8-80177 | 3/1996 | Japan . |

OTHER PUBLICATIONS

Database WPI Section, Derwent Publications Ltd., London, Great Britain: Class D13. (1996).

Kometani, Takashi et al., "Synthesis of Hesperidin Glycosides by Cyclodextrin Glucanotransferase and Stabilization of the Natural Pigments", *Nippon Shokuhin Kagaku Kogaku Kaishi*, vol. 42, No. 5, pp. 376–382 (1995).

*Primary Examiner*—Francisco Prats
*Attorney, Agent, or Firm*—Webb Ziesenheim Logsdon Orkin & Hanson, P.C.

[57] ABSTRACT

The present process for producing a high α-monoglucosyl hesperidin content product is characterized in that it comprises the steps of contacting glucoamylase and α-L-rhamnosidase simultaneously or randomly with a solution containing α-glucosyl hesperidin and hesperidin to obtain a mixture; crystallizing and separating α-monoglucosyl hesperidin in and from the mixture; and collecting the resulting α-monoglucsyl hesperidin. From solutions containing α-glucosyl hesperidin and hesperidin, the present invention facilitates the production of a high α-monoglucosyl hesperidin content product which does not substantially contain hesperidin, β-monoglucosyl hesperetin, and hesperetin, and has an extremely-superior water-solubility.

8 Claims, No Drawings

PROCESS FOR PRODUCING α-MONOGLUCOSYL HESPERIDIN-RICH SUBSTANCE

TECHNICAL FIELD

The present invention relates to a process for producing a high α-monoglucosyl hesperidin content product, and more particularly to a process for producing a high α-monoglucosyl hesperidin content product, which comprises the steps of treating a solution containing α-glucosyl hesperidin and hesperidin to crystallize and separate α-monoglucosyl hesperidin, and collecting the resulting α-monoglucosyl hesperidin.

BACKGROUND ART

As shown in the following Formula [I], hesperidin is a compound where rutinose (L-rhamnosyl-(α 1→6)-glucose) binds to the hydroxyl group at the C-7 in hesperetin (3',5,7-trihydroxy-4'-metoxyflavanone) via the β-linkage.

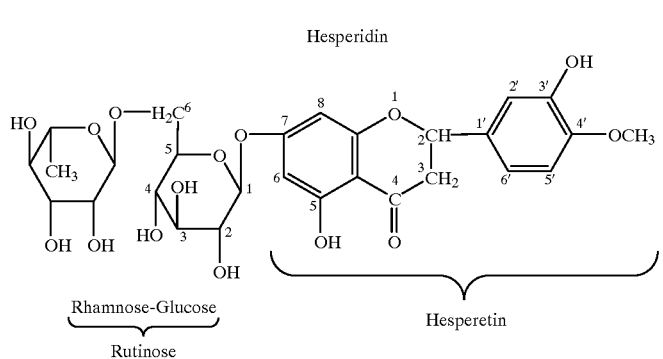

Formula [I]

Hesperidin is present in immature fruit skins of citruses and used in pharmaceuticals, cosmetics, etc., as a vitamin P that has physiological functions such as capillary protestant, hemorrhagic prevention, blood-pressure control, etc. Hesperidin dissolves in aqueous alkaline solutions but not substantially in water and acids. Because only about one gram hesperidin dissolves in 50 l water (about 0.002 w/v %) at ambient temperature, it easily causes cloudiness in the liquid parts of canned foods with only a slight amount thereof to deteriorate the products' value.

There have been proposed methods to prevent such cloudiness in liquids induced by hesperidin. For example, Japanese Laid-Open Publication No. 7,593/91 discloses a process for producing an enzyme-treated hesperidin with improved water-solubility, which comprises the steps of contacting hesperidin with a saccharide-transferring enzyme (an enzyme having α-glucosyl-transferring activity) in the presence of partial starch hydrolyzates (α-glucosyl saccharides) to form α-glucosyl hesperidin as shown by the following Formula [II]:

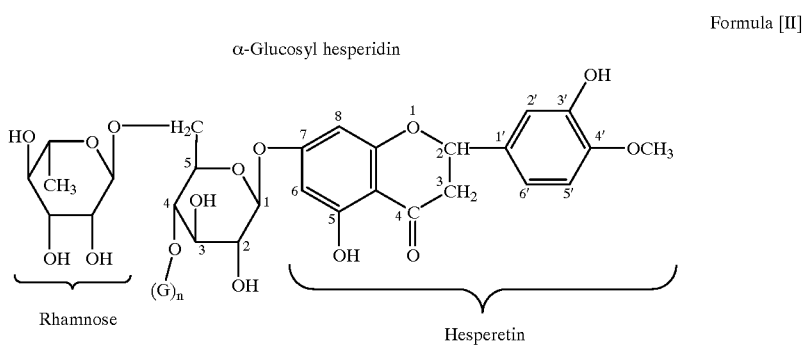

Formula [II]

As shown in the above Formula [II], the α-glucosyl hesperidin is a compound where glucose(s) ($G_n$, n=1-20) successively bind(s) via the α-1,4 linkage to the C-4 of the glucose in hesperidin in Formula [I], or a mixture of such α-glucosyl hesperidins having different numbers of glucoses.

In the enzymatic reaction system, 40–80% hesperidin contained in a material solution is converted into α-glucosyl hesperidin by the enzyme treatment, while 20–60% hesperidin still remains intact free of reaction. The coexistence of α-glucosyl hesperidin increases the solubility of intact hesperidin in aqueous solutions, but a higher proportion of the intact hesperidin to the α-glucosyl hesperidin results in an insolubilization and crystallization of intact hesperidin within a relatively short period of time.

Although it can be proposed a method for adding gelatinizers such as carboxymethyl cellulose (CMC) to aqueous solutions containing hesperidin to increase the viscosity of the solutions as a means to prevent the crystallization of intact hesperidin, it could not be a general method because such an addition of the gelatinizers will not be acceptable in view of product image and should not be used in export products.

Also there exists a method for delaying the crystallization of intact hesperidin by crystallizing intact hesperidin and filtering the mixture to separate and remove the crystallized hesperidin in order to lower the proportion of the intact hesperidin to α-glucosyl hesperidin. Even with the method, intact hesperidin does crystallize after a relatively long period of time as a demerit, and therefore it could not be a substantial solution.

There still exists a method which comprises a step of collecting only a fraction of α-glucosyl hesperidin from aqueous solutions containing α-glucosyl hesperidin and intact hesperidin by a technique such as chromatographic fractionation to obtain a desired product for use. The method, however, results in a cost increase and is far from a beneficial method.

The present inventors continued studying to solve the problems in the prior art and found that an enzyme-treated hesperidin, which has extremely-increased water-solubility and does not substantially cause cloudiness even after a relatively long period of time, is obtainable by contacting an enzyme having α-L-rhamnosidase activity with solutions containing α-glucosyl hesperidin and intact hesperidin to hydrolyze intact hesperidin to release rhamnose and to be hydrolyzed into β-monoglucosyl hesperetin in the following chemical formula [III], while α-glucosyl hesperidin is remained substantially unchanged:

Takashi KOMETANI, Yoshinobu TERADA et al. disclosed in *Nippon Shokuhin Kagaku Kogaku Kaishi (Japan Food Science Technology)*, Vol. 42, No. 5, pp. 376–382 (May of 1995), titled "*Formation of Sugar Derivatives of Hesperidin and Stabilization of Natural Pigments by Cyclodextrin Glucanotransferase*", that they found that: After reacting hesperidin as a saccharide acceptor, β-cyclodextrin (β-CD) as a saccharide donor, and CGTase as a saccharide-transferring enzyme for obtaining sugar derivatives of hesperidin designated as Hsp-Gn, the action of (α-rhamnosidase on the sugar derivatives during the purification step thereof results in a selective hydrolysis of intact hesperidin, and this facilitates the effective separation of the sugar derivatives in a purified form from the intact hesperidin on column chromatography using a column packed with "SEPHADEX LH-20"; and that they succeeded to inhibit the color fading of natural pigments induced by ultraviolet by adding the purified sugar derivatives.

However, the method of the above literature is to prepare α-monoglucosyl hesperidin in the formula [IV] by separating concomitant hesperetin using "AMBERLITE XAD-16" and separating a-monoglucosyl hesperidin and α-diglucosyl hesperidin from a mixture of the resulting β-monoglucosyl hesperetin, α-monoglucosyl hesperidin, and α-diglucosyl hesperidin by using an expensive column chromatography. The method is substantially impossible to selectively separate a high α-monoglucosyl hesperidin content product in a satisfactorily-high yield. Thus, the preparation of such a product in a simpler manner and at a lower cost will give a much more expectation of being widely used in pharmaceuticals, cosmetics, food additives, etc.

Formula [III]

β-Monoglucosyl hesperetin

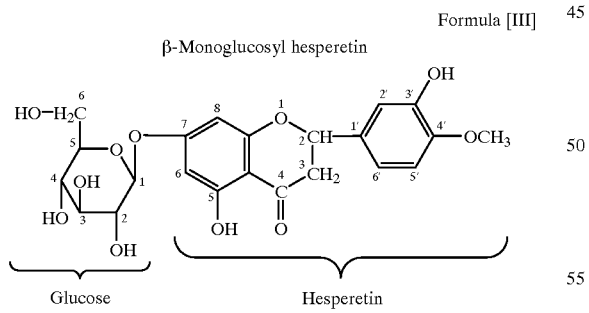

Glucose    Hesperetin

α-Monoglucosyl hesperidin

Formula IV

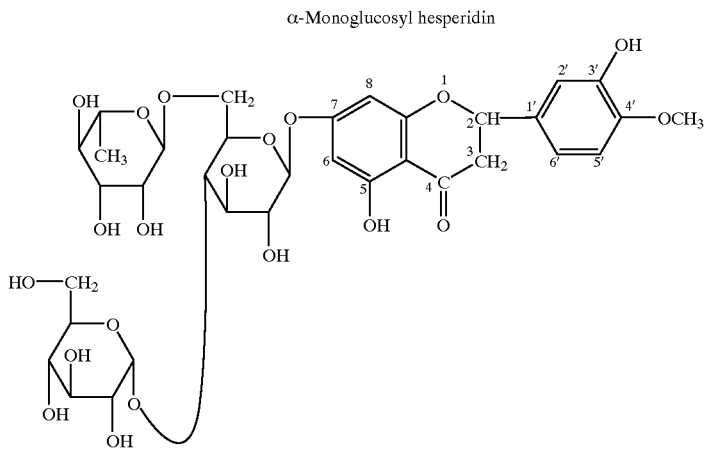

The above-identified Japanese Laid-Open Publication No. 7,593/91 discloses a method which comprises the steps of contacting glucoamylase (EC 3.2.1.3) with a mixture solution of α-glucosyl hesperidin and hesperidin to hydrolyze the α-glucosyl hesperidin to α-monoglucosyl hesperidin, feeding the mixture to a column packed with "DIAION HP-20", washing the column with water, and collecting a fraction of α-monoglucosyl hesperidin while increasing step-wisely the concentration of ethanol in the aqueous system. Even the above-mentioned method could substantially be impossible to supply a high α-monoglucosyl hesperidin content product at a satisfactorily lower cost.

After further study the present inventors found that α-monoglucosyl hesperidin is effectively separated and collected from the mixture obtained in the below by using a method which comprises the steps of either contacting glucoamylase and α-L-rhamnosidase (EC 3.2.1.40) or contacting glucoamylase, α-L-rhamnosidase, and β-D-glucosidase (EC 3.2.1.21) with a solution containing α-glucosyl hesperidin and hesperidin; crystallizing the formed α-monoglucosyl hesperidin in the resulting mixture; separating the crystals; and collecting the separated crystals.

The present invention produces a high α-monoglucosyl hesperidin content product in an extremely high yield with only applying a solid-separation method to a starting mixture to separate crystallized α-monoglucosyl hesperidin.

As a method for preventing the cloudiness of syrups in canned mandarin oranges, a method for improving the water solubility of hesperidin, which comprises contacting an enzyme having α-L-rhamnosidase activity with hesperidin to convert it into β-monoglucosyl hesperetin, is employed on an industrial scale.

However, there has been no indication of a method like the present invention which comprises the steps of either contacting glucoamylase and α-L-rhamnosidase or contacting an enzyme preparation having glucoamylase, α-L-rhamnosidase, and β-D-glucosidase activities with solutions containing α-glucosyl hesperidin and intact hesperidin to hydrolyze the α-glucosyl hesperidin to form α-monoglucosyl hesperidin, where leaving the rhamnose residue in the α-glucosyl hesperidin unchanged and leaving only one glucose residue among the glucose residues (Gn) that are linked to the C-4 of the glucose residue in the α-glucosyl hesperidin, and to hydrolyze the rhamnose residue in hesperidin into β-monoglucosyl hesperetin, i.e., 7-O-β-monoglucosyl hesperetin, and optionally further to hydrolyze the β-glucose residue in the β-monoglucosyl hesperetin into hesperetin; effectively crystallizing and separating only the α-monoglucosyl hesperidin; and collecting the resulting α-monoglucosyl hesperidin.

Japanese Laid-Open Publication No. 80,177/96 discloses a method for preventing the crystallization of hesperidin by the addition of solubilized hesperidin to aqueous solutions containing hesperidin, where the solubilized hesperidin is a compound that is composed of one to ten and several glucose residues bound to the C-4 of the glucose residue in hesperidin via the α-1,4 linkage and that is producible by contacting saccharide-transferring enzymes with hesperidin in the presence of cyclodextrins, etc., where the saccharide-transferring enzymes are, for example, CGTase or 1,4-α-D-glucan; 1,4-α-D-(1,4-glucano)-transferase (EC 2.4.1.19), and more concretely a saccharide-transferring enzyme prepared from a culture of Bacillus A2-5a strain.

The above publication, however, simply discloses a technical art to prevent the crystallization of hesperidin in products containing the hesperidin by admixing solubilized hesperidin with intact hesperidin. Products, obtained by the method and disclosed in the publication, are mixtures of α-glucosyl hesperidin and hesperidin, meaning that they still contain intact hesperidin, and as a demerit they easily and gradually cause cloudiness in the liquid parts of canned products. To solve this problem, α-monoglucosyl hesperidin and α-diglucosyl hesperidin fractions are collected and used in an Example of the above-identified publication. However, economical collection of the two fractions involves technical difficulties.

The present invention solves the above problems in the prior art and is to provides a method for collecting a high α-monoglucosyl hesperidin content product by treating solutions containing α-glucosyl hesperidin and hesperidin with a relatively simpler treatment.

SUMMARY OF THE INVENTION

The process for producing a high α-monoglucosyl hesperidin content product according to the present invention comprises the steps of: separating and collecting α-monoglucosyl hesperidin from a solution (a) identified in the below by the method I or II, where the method I comprises the steps of contacting glucoamylase and α-L-rhamnosidase simultaneously or randomly with a solution containing α-glucosyl hesperidin and hesperidin as the solution (a), and crystallizing and separating α-monoglucosyl hesperidin in and from the resulting mixture as an enzyme reaction solution (b-1); and the method II comprises the steps of contacting enzyme preparations having glucoamylase, α-L-rhamnosidase, and β-D-glucosidase activities simultaneously or randomly with the solution (a), and crystallizing and separating α-monoglucosyl hesperidin in and from the resulting mixture as an enzyme reaction solution (b-2).

In a preferred embodiment according to the present invention, prior to the crystallization and separation of α-monoglucosyl hesperidin, the above enzyme reaction solutions are preferably allowed to contact with porous adsorption resins to adsorb thereupon α-monoglucosyl hesperidin, β-monoglucosyl hesperetin, hesperetin, etc., followed by washing the resins with water to elute dextrins, etc., and desorbing α-monoglucosyl hesperidin, β-monoglucosyl hesperetin, and hesperetin from the resins with organic solvents such as alcohols; and optionally the organic solvents contained in the eluates are preferably removed. Furthermore, in a preferred embodiment according to the present invention, α-monoglucosyl hesperidin contained in the eluates is preferably crystallized in lower alcohols such as methanol, and then collected separately.

The present invention facilitates the preparation of a high α-monoglucosyl hesperidin content product which contains substantially no hesperidin, β-monoglucosyl hesperetin, and hesperetin and has an extremely high water solubility.

Detailed Description

The following is a detailed description of the process for producing a high α-monoglucosyl hesperidin content product according to the present invention.

In the present separation method or process for producing a high α-monoglucosyl hesperidin content product, glucoamylase, α-L-rhamnosidase, and β-D-glucosidase are simultaneously or randomly allowed to contact with a solution containing α-glucosyl hesperidin and hesperidin, where the β-D-glucosidase should not be used prior to the glucoamylase and α-L-rhamnosidase, and then α-monoglucosyl hesperidin is obtained after crystallized in and separated from the resulting enzyme-treated solution.

First, solutions containing α-glucosyl hesperidin and hesperidin are described:

Solution Contianing α-Glucsyl Hesperidin and Hesperidin

Any solutions can be used in the above enzyme treatment as long as they contain α-glucosyl hesperidin and hesperidin independently of their proportions and concentrations. Preferably used are those containing 0.1–30% by weight, and more preferably 1–10% by weight of α-glucosyl hesperidin; those containing 0.02–15% by weight, and more preferably 0.2–5% by weight of hesperidin; and those with a proportion in the range of 100 to 1–200, and preferably in the range of 100 to 1–20 by weight with respect to the weight proportion of α-glucosyl hesperidin to hesperidin.

Examples of such solutions containing α-glucosyl hesperidin and hesperidin are the following Solutions 1 and 2:

Solution 1: A solution containing α-glucosyl hesperidin and intact hesperidin which is obtainable by, as disclosed in Japanese Laid-Open Publication No. 7,593/91, contacting a saccharide-transferring enzyme (an enzyme having α-glucosyl-transferring activity) with hesperidin in the presence of a partial starch hydrolyzate (an α-glucosyl saccharide).

Solution 2: A solution which is obtainable by crystallizing hesperidin in a solution containing α-glucosyl hesperidin prepared similarly as above, and separating and removing hesperidin by filtration, etc., to lower the percentage of hesperidin to α-glucosyl hesperidin.

Enzyme Preparations Having activities of Glucoamylase, α-L-rhamnosidase, and β-D-glucosidase Any glucoamylase, α-L-rhamnosidase, and β-D-glucosidase can be used in the present invention as long as they have the respective activities:

Examples of glucoamylase include commercially available enzyme preparations, capable of cutting the α-1,4 glucosidic linkages by glucose units, such as "GLUCZYME NL4,2" and "CELLULASE A <AMANO> 3", both of which are products of Amanoseiyaku Co., Ltd., Tokyo, Japan; "GLUCOZYME", a product of Nagase Biochemicals, Ltd., Kyoto, Japan; "UNIASE 30", a product of Yakult Honsha Co., Ltd, Tokyo, Japan; and "NARINGINASE", a product of Tanabe Seiyaku Co., Ltd., Tokyo, Japan.

Examples of α-L-rhamnosidase are commercially available enzyme preparations such as "HESPERIDINASE" and "NARINGINASE", both of which are products of Tanabe Seiyaku Co., Ltd., Tokyo, Japan; and "CELLULASE A <AMANO> 3", a product of Amanoseiyaku Co., Ltd., Tokyo, Japan; and "HESPERIDINASE" can be used preferably.

Examples of β-D-glucosidase include commercially available enzyme preparations such as "CELLULASE A <AMANO> 3", a product of Amanoseiyaku Co., Ltd., Tokyo, Japan.

Among these enzyme preparations, those having glucoamylase activity can be used in an amount of about 5 0.01 to about 10 parts by weight, and more preferably about 0.1 to about one part by weight with respect to 100 parts by weight of α-glucosyl hesperidin in the above-identified solutions containing α-glucosyl hesperidin and hesperidin.

The enzyme preparations having α-L-rhamnosidase activity can be preferably used in an amount of about 0.05 to about 50 parts by weight, and more preferably about 1.5 to about 15 parts by weight with respect to 100 parts by weight of hesperidin in the above-identified solutions containing α-glucosyl hesperidin and hesperidin.

The enzyme preparations having β-D-glucosidase activity can be preferably used in an amount of about 0.01 to about 20 parts by weight, and more preferably about 0.1 to about 10 parts by weight with respect to 100 parts by weight of hesperidin in the above-identified solutions containing α-glucosyl hesperidin and hesperidin. In the case of using commercially available enzyme preparations, having at least two types of enzyme activities from among glucoamylase, α-rhamnosidase, and β-D-glucosidase activities, such as "CELLULASE A <AMANO> 3", a product of Amanoseiyaku Co., Ltd., Tokyo, Japan, the dose thereof can be appropriately changed.

When acting on α-glucosyl hesperidin and hesperidin in the aforesaid solutions, these enzyme preparations can be usually incubated at pH of 3–7, and preferably pH of 3–4; at temperatures of 40–70° C., and preferably 50–60° C; and for about 0.5 to about 72 hours, and preferably about 6 to about 48 hours.

Enzyme treatment with α-L-rhamnosidase such as hesperidinase does not substantially act on α-glucosyl hesperidin when the above-identified solutions containing α-glucosyl hesperidin and hesperidin are treated under the above conditions.

The α-glucosyl hesperidin is, however, hydrolyzed by glucoamylase in a manner such that the glucose residues of "n" in number, an integer of one to ten and several, successively linked to the glucose at the C-7 of the hesperetin skeleton in the α-glucosyl hesperidin via the α-1,4 linkages, are hydrolyzed, while one glucose residue is being left, into α-monoglucosyl hesperidin as shown by the above-identified Chemical Structure [II] where "n" is one.

When acting on α-glucosyl hesperidin including α-monoglucosyl hesperidin, β-D-glucosidase does not substantially hydrolyze them.

While α-L-rhamnosidase acts on hesperidin to hydrolyze the rhamnose residue in the compound into β-monoglucosyl hesperetin, i.e., 7-O-β-monoglucosyl hesperetin.

Successive action of β-D-glucosidase on the above β-monoglucosyl hesperetin results in a hydrolysis of the β-glucose residue, linked to the C-7 of the hesperetin skeleton in the β-monoglucosyl hesperetin, to form substantially water-insoluble hesperetin.

Therefore, the systematic order of adding the above-identified enzyme preparations to the solutions containing α-glucosyl hesperidin and hesperidin according to the present invention is as follows: Glucoamylase and α-L-rhamnosidase can be randomly or simultaneously allowed to act on solutions containing α-glucosyl hesperidin and hesperidin because the conversion of α-glucosyl hesperidin and hesperidin into α-monoglucosyl hesperidin and β-monoglucosyl hesperetin, respectively, is effected randomly or simultaneously in the method I, where glucoamylase and α-L-rhamnosidase are allowed to act on the solutions containing α-glucosyl hesperidin and hesperidin, and the formed α-monoglucosyl hesperidin is crystallized in and collected from the resulting mixtures, i.e., enzyme reaction mixtures. The contents of ingredients in the resulting enzyme reaction mixtures are 0.5 part by weight or lower of β-monoglucosyl hesperetin and 0.1 part by weight or lower of respective hesperidin and hesperetin to one part by weight of α-monoglucosyl hesperidin. The enzyme reaction mixtures may contain other ingredients such as saccharides in an amount of one part by weight or more to one part by weight of the α-monoglucosyl hesperidin in the reaction mixtures.

The method II, which comprises the steps of contacting glucoamylase, α-L-rhamnosidase, and β-D-glucosidase with solutions containing α-glucosyl hesperidin and hesperidin randomly or simultaneously, and crystallizing and collecting the formed α-monoglucosyl hesperidin in and from the resulting mixtures, i.e., enzyme reaction mixtures, includes the following methods:

1. A method where glucoamylase, α-L-rhamnosidase, and β-D-glucosidase are simultaneously added to the solutions;

2. A method where glucoamylase and α-L-rhamnosidase are added to the solutions for enzymatic reaction before the addition of β-D-glucosidase;

3. A method where glucoamylase and α-L-rhamnosidase are randomly added to the solutions for enzymatic reaction before the addition of β-D-glucosidase; and 4. A method where α-L-rhamnosidase and β-D-glucosidase are allowed to act on the solutions to proceed the conversion of hesperidin into hesperetin in advance before the action of glucoamylase.

In any methods the enzymes can be added to the solutions simultaneously or gradually by small portions.

The contents of ingredients in the resulting enzyme reaction mixtures are 0.4 part by weight or lower of hesperetin and 0.1 part by weight or lower of respective β-monoglucosyl hesperetin and hesperidin to one part by weight of α-monoglucosyl hesperidin. The reaction mixtures may contain at least one part by weight or more of other ingredients such as saccharides to one part by weight of α-monoglucosyl hesperidin.

In the method I among the above methods according to the present invention, α-L-rhamnosidase and glucoamylase are preferably allowed to act on the solutions in this order.

In the method II, glucoamylase and β-D-glucosidase should preferably be allowed to act on the solutions after the action of α-L-rhamnosidase in view of the reaction efficiency.

Collection of α-monoglucosyl Hesperidin

As described above, according to the present invention, α-monoglucosyl hesperidin is collected from enzyme-treated solutions containing α-monoglucosyl hesperidin or solutions containing α-monoglucosyl hesperidin obtained by enzyme treatment, which are prepared by treating solutions containing α-glucosyl hesperidin and hesperidin with enzymes.

To collect α-monoglucosyl hesperidin from enzyme-treated solutions, the method I employs a mixing of lower alcohols with enzyme-treated solutions which contain, based on one part by weight of α-monoglucosyl hesperidin, 0.5 part by weight or lower of β-monoglucosyl hesperetin, 0.1 part by weight or lower of respective hesperidin and hesperetin, and one part by weight or more of saccharides and other ingredients; and similarly the method II employs a mixing of lower alcohols with enzyme-treated solutions which contain, based on one part by weight of α-monoglucosyl hesperidin, 0.4 part by weight or lower of hesperetin, 0.1 part by weight or lower of respective β-monoglucosyl hesperetin and hesperidin, and one part by weight or more of other ingredients such as saccharides. Prior to the methods, free saccharides in the enzyme-treated solutions may preferably be removed. Any methods can be used for such purpose as long as they effectively remove the saccharides, and those using porous adsorption resins can be used easily.

Non-polar resins such as HP-20, HP-50, XAD-2, etc., and resins with intermediate polarity such as XAD-7, etc., can be preferably used as the porous adsorption resins. In these methods, the porous adsorption resins are first packed in columns and activated by high-concentration aqueous ethanol solutions, etc., then the above enzyme-treated solutions containing α-monoglucosyl hesperidin are fed to the columns at temperatures of 10–60° C. to contact with the resins and to adsorb thereupon α-monoglucosyl hesperidin, β-monoglucosyl hesperetin, hesperetin, etc.

Thereafter, the columns are washed with about one-fold to about four-fold volumes of water with respect to the resins by volume to remove impurities comprising free saccharides mainly, and then fed with eluants such as alcohols and alcohol-water solvent systems (alcohol/water=50–100/25-1 by volume) at temperatures of 10–60° C. to elute the α-monoglucosyl hesperidin, β-monoglucosyl hesperetin, hesperetin, etc., adsorbed on the resins.

The method I provides an eluate which comprises, based on one part by weight of α-monoglucosyl hesperidin, 0.5 part by weight or lower of β-monoglucosyl hesperetin, 0.1 part by weight or lower of hesperidin and hesperetin, and 0.1 part by weight or lower of other ingredients such as saccharides; and the method II provides an eluate which comprises, based on one part by weight of α-monoglucosyl hesperidin, 0.4 part by weight or lower of hesperetin, 0.1 part by weight or lower of β-monoglucosyl hesperetin and hesperidin, and 0.1 part by weight or lower of other ingredients such as saccharides.

The above alcohols include lower alcohols of 1 to 5 carbon atoms such as methanol, ethanol, propanol, butanol, etc.

The α-monoglucosyl hesperidin in the eluates is crystallized in lower-alcohol solvent systems, subjected to solid-liquid separation, and collected to obtain a high α-monoglucosyl hesperidin content product.

Such a process was made based on the finding of dynamics that α-monoglucosyl hesperidin easily dissolves in heated lower alcohols but easily crystallizes therein when the alcohols are cooled down to temperatures below ambient temperature, for example, 15–25° C.; and that β-monoglucosyl hesperetin easily dissolves in lower alcohols and does not substantially crystallize even when the alcohols are cooled down to temperatures below ambient temperature.

The crystallization and separation processes of the methods I and II are respectively described in detail in the below. In both methods, the above enzyme-treated eluate should preferably be dried before their dissolution in the above lower alcohols.

Crystallization and Collection Procedure Method I

A dry product, which may contain, based on one part by weight of α-monoglucosyl hesperidin, 0.5 part by weight or lower of β-monoglucosyl hesperetin, 0.1 part by weight or lower of respective hesperidin and hesperetin, and 0.1 part by weight or lower of other ingredients such as saccharides, is dissolved in a lower alcohol, preferably in methanol. Then, methanol is added thereto in an amount of 0.2–20 ml, preferably 1–10 ml based on one gram of the dry product, and the resulting mixture is heated at temperatures of 20–120° C., preferably 60–90° C. to dissolve the product.

Thereafter, the resulting solution is cooled, for example, by cooling the solution up to temperatures from below ambient temperature to over the melting points of the alcohols or allowing the solution to stand at ambient temperature to crystallize almost α-monoglucosyl hesperidin only. In such a case of cooling the solution, treatment of adding thereto a small amount of previously pulverized α-monoglucosyl hesperidin as a seed more accelerates the crystallization.

Thereafter, a high α-monoglucosyl hesperidin content product is obtained by applying solid-liquid separation such as centrifugation.

In the separation, washing of the resulting α-monoglucosyl hesperidin crystals with lower alcohols can yield a high α-monoglucosyl hesperidin content product enriched with the α-monoglucosyl hesperidin.

Method II

A high α-monoglucosyl hesperidin content product is obtainable from the dry product in the below by a process similar to the method I except for using a dry product which may contain, based on one part by weight of α-monoglucosyl hesperidin, 0.4 part by weight or lower of hesperetin, 0.1 part by weight or lower of respective β-monoglucosyl hesperetin and hesperidin, and 0.1 part by weight or lower of other ingredients such as saccharides.

It is most preferable that the high α-monoglucosyl hesperidin content products, named as (a) and (b), obtained in the methods I and II, respectively, should contain at least 85%, and preferably at least 95% by weight of α-monoglucosyl hesperidin. It is most preferable that any of hesperidin, β-monoglucosyl hesperetin, i.e., 7-O-β-monoglucosyl hesperetin, and hesperetin should not coexist with α-gluosyl hesperidin. However, even in such cases of containing the above concomitants, the content of hesperidin coexisting with the α-monoglucosyl hesperidin should preferably be 0.10 part by weight or lower, more preferably 0.05 part by weight or lower, and most preferably 0–0.01 part by weight based on one part by weight of the α-monoglucosyl hesperidin; and the content of β-monoglucosyl hesperetin, i.e., 7-O-β-monoglucosyl hesperetin should preferably be 0.10 by weight or lower, more preferably 0.05 part by weight or lower, and most preferably 0–0.02 part by weight based on one part by weight of the α-monoglucosyl hesperidin. The content of hesperetin should preferably be 0.10 part by weight or lower, more preferably 0.05 part by weight or lower, and most preferably 0–0.01 part by weight based on one part by weight of the α-monoglucosyl hesperidin.

The above products (a) and (b) have superior water-solubility; they form substantially no visible floc such as crystallization of hesperidin, hesperetin, etc., when observed macroscopically even after a four-week standing of solutions containing 30% by weight of the products, on a dry solid basis (d.s.b.), at ambient temperature, e.g., 250°C.

When taken by living bodies, the α-monoglucosyl hesperidin, contained in high α-monoglucosyl hesperidin content products, is acted by the in vivo enzymes to be converted back into hesperidin as a starting material. A function as vitamin P can be exerted. In this case, the combination use of vitamin C and α-monoglucosyl hesperidin or its high content product can exert synergistic effect with respect to vitamin P activity such as the enhancement of capillary resistance.

These high α-monoglucosyl hesperidin content products can be suitably used as color-deterioration-preventing agents for natural pigments.

In such a case, the high α-monoglucosyl hesperidin content products can be preferably used in color-deterioration-preventing for natural pigments, in an amount of 0.001–0.2% by weight, preferably 0.005–0.1 part by weight, and more preferably 0.01–0.05 part by weight to the sample colored with natural pigments.

Explaining in more detail, hesperidin has almost no color because of its characteristic ultraviolet absorption spectrum and insubstantial distinctive absorption in visible region, and has been tried to be used in the prevention of pigments susceptible to fading by ultraviolet, particularly in the prevention of natural pigments. However, hesperidin could not exert its effect due to its insubstantial water-solubility. Even with an enzyme-treated hesperidin with increased water-solubility, such a conventional product has fear of causing crystallization and sedimentation of intact hesperidin, and this deteriorates products image as a problem of actual use.

While the high α-monoglucosyl content product according to the present invention is water soluble and substantially free of forming sedimentation, it can be widely used to prevent fading of natural pigments. Particularly, the present product can be effectively used for carotenoid pigments such as papurica, β-carotenoid, and astaxanthin; flavonoid pigments such as rinds of grapes and safflower yellow; and others of beet red, turmeric pigment, gardenia blue, and beni-koji pigment.

In this case, the combination use of the high α-monoglucosyl content product and either or both of enzyme-treated rutin and L-ascorbic acid or sodium L-ascorbate attains a synergistic effect in the prevention of fading of natural pigments.

When used to prevent cloudiness of canned mandarin oranges, the high α-monoglucosyl hesperidin content product is preferably added based on one part by weight of hesperidin as intact hesperidin, contained in the mandarin oranges and syrups or liquid parts in the canned products, 0.1–10 parts by weight, preferably 0.1–2 parts by weight, and more preferably 0.1–1 part by weight.

The high α-monoglucosyl hesperidin content product can be used to prevent cloudiness of citrus fruit beverages containing hesperidin, e.g., Satsuma mandarins, navel oranges, other oranges, etc., an amount of the high α-monoglucosyl hesperidin content product is 0.01–10 parts by weight, preferably 0.1–2 part by weight, and more preferably 0.1–1 part by weight based on one part by weight of hesperidin or intact hesperidin, contained in the liquid parts.

Furthermore, the high α-monoglucosyl hesperidin content product has properties of a characteristic ultraviolet absorption spectrum and an extremely light color, and therefore it can be used in cosmetics as an ultraviolet absorber/interceptor, etc.

EFFECT OF THE INVENTION

From solutions containing α-glucosyl hesperidin and hesperidin, the present invention effectively and easily produces a high α-monoglucosyl hesperidin content product which does not substantially contain hesperidin, β-monoglucosyl hesperetin, hesperetin, etc., which has satisfactory water-solubility, and does not cause cloudiness or crystals.

EXAMPLE

With reference to the following Examples, the process for producing high α-monoglucosyl hesperidin content products according to the present invention is explained in more detail, but this invention should not be restricted thereby.

The symbol "%" used in the below means "% by weight", unless it contradicts the desired meaning.

Referential Example 1

50.0 g hesperidin was dissolved in 0.9 l of 0.25-N sodium hydroxide (NaOH), and then 150 g dextrin with DE (dextrose equivalent) 8 was admixed with and dissolved in the resulting solution.

The solution was adjusted to pH 9.0 with 4-N sulfuric acid, mixed with 15 units/g dextrin of cyclomaltodextrin glucanotransferase derived from a microorganism of the species *Bacillus stearothermophilus*, commercialized by Hayashibara Biochemical Laboratories, Inc., Okayama, Japan, adjusted to pH 8.3 by the addition of 4-N sulfuric acid while heating up to 60° C., and enzymatically reacted for six hours.

Thereafter, the mixture solution was adjusted to pH 7.0 by the addition of 4-N sulfuric acid, heated to 68° C., and enzymatically reacted for 40 hours.

After completion of the enzymatic reaction, the remaining enzyme was inactivated by heating and filtered to obtain an enzyme-treated hesperidin solution as Solution A.

HPLC (high-performance liquid chromatography) analysis of Solution A under the conditions given in the below revealed that 72% hesperidin in the material solution was converted into α-glucosyl hesperidin and the resting 28% hesperidin was remained intact.

Conditions for HPLC Analysis

Column: C18

Eluant: Methanol:water:acetic acid=30:65:5

Detection: 280 nm

Temperature: 40° C.

Flow rate: 0.5 ml/min

Conformation of Hesperidin, β-Monoglucosyl Hesperetin, α-Monoglucosyl Hesperidin, α-Glucosyl Hesperidin. etc.

Hesperidin, β-monoglucosyl hesperetin, α-monoglucosyl hesperidin, α-glucosyl hesperidin, etc., were confirmed by the following methods:

1. Hesperidin:

Identify a sample using hesperidin in a reagent grade commercialized by Tokyo Kasei Organic Chemicals, Tokyo, Japan.

2. β-Monoglucosyl hesperetin:

Contacting α-L-rhamnosidase with hesperidin in a reagent grade commercialized by Tokyo Kasei Organic Chemicals, Tokyo, Japan, and analyze the reaction mixture on HPLC under the above analysis conditions. Collect a single peak fraction with R.T. (retention time)=12.13 after a hesperidin fraction with R.T.=10.90, and hydrolyze the single peak fraction for detecting glucose. Confirm the ultraviolet absorption spectrum for the single peak fraction to be coincided with that of hesperidin for identifying the sample as β-monoglucosyl hesperetin or hesperetin-7-glucoside.

3. α-Monoglucosyl hesperidin, α-glucosyl hesperidin:

Analyze a reaction mixture, obtained by using hesperidin in a reagent grade commercialized by Tokyo Kasei Organic Chemicals, Tokyo, Japan, on HPLC under the above analysis conditions. Confirm each peak in ultraviolet absorption spectrum of the reaction mixture to be coincided with those of hesperidin. Contact glucoamylase with the reaction mixture, and analyze the resulting mixture on HPLC under the above analysis conditions. As a result, either of peaks resulted in a single peak with R.T.=10.34 detected before a peak of hesperidin with R.T.=10.90.

Collect the fraction with R.T.=10.34, contact α-glucosidase (EC 3.2.1.20) with the fraction for hydrolyzing the contents, and confirm the formation of glucose and hesperidin. A peak with R.T.=10.34 was regarded as a fraction of α-monoglucosyl hesperidin, and the peak plus other peaks with R.T. values smaller than that of the peak were regarded as a fraction of α-glucosyl hesperidin.

Method for Weighing Hesperidin, β-Monoglucosyl Hesperetin, α-Monoglucosyl Hesperidin, α-Glucosyl Hesperidin, etc.

The following methods were used to weigh hesperidin, β-monoglucosyl hesperetin, α-monoglucosyl hesperidin, α-glucosyl hesperidin, etc.

1. Hesperidin:

Analyze a sample on HPLC and calculate the weight based on hesperidin in a reagent grade commercialized by Tokyo Kasei Organic Chemicals, Tokyo, Japan.

2. β-Monoglucosyl hesperetin:

Analyze a sample on HPLC and calculate the weight by molecular conversion based on hesperidin in a reagent grade commercialized by Tokyo Kasei Organic Chemicals, Tokyo, Japan.

3. α-Monoglucosyl hesperidin:

Analyze a sample on HPLC and calculate the weight by molecular weight conversion based on hesperidin in a reagent grade commercialized by Tokyo Kasei Organic Chemicals, Tokyo, Japan.

4. α-Glucosyl hesperidin fraction:

Dissolve 1.0 g of the dried fraction, as a sample, in 50 ml water, feed the solution at SV (space velocity) =1 to a column packed with 100 ml of XAD-7 (a resin, which had been previously activated by a high-concentrated aqueous ethanol solution and washed sufficiently with water), wash the column with water, and feed 200 ml of 50% aqueous ethanol solution to the column for elution. Remove ethanol from the eluate, and concentrate and dry the resulting eluate before weighing. When hesperidin and β-monoglucosyl hesperetin in the contents were detected on HPLC analysis, the weight of the fraction of α-glucosyl hesperidin was calculated by reducing the weights of these compounds calculated based on the above methods 1 and 2.

Example 1

Two grams of "RESPERIDINASE NO.2", a hesperidinase preparation commercialized by Tanabe Seiyaku Co., Ltd., Tokyo, Japan, was added to the Solution A in Referential Example 1, adjusted to pH 4 using 4-N sulfuric acid, enzymatically reacted at 55° C. for 24 hours, admixed with 1.0 g of "GLUCOZYME", a glucoamylase preparation commercialized by Nagase Biochemicals, Ltd., Kyoto, Japan, and further enzymatically reacted at 55° C. for 24 hours.

After completion of the enzymatic reaction, the reaction mixture was incubated at 90° C. for 20 min to inactivate the remaining enzyme and filtered to obtain an enzyme-treated hesperidin solution as Solution B. HPLC analysis of Solution B under the conditions described in Referential Example 1 revealed that most of the α-glucosyl hesperidin in Solution B was converted into α-monoglucosyl hesperidin, and most (99% or more) of the intact hesperidin in Solution B was converted into β-monoglucosyl hesperetin, i.e., hesperetin monoglucoside.

Solution B was passed through a column packed with 1.5 l of "XAD-7", a porous adsorption resin with intermediate polarity, which had been activated by high-concentrated aqueous ethanol solution, followed by washing the column with two-fold bed-volumes of water and desorbing the ingredients adsorbed on the resin using three liters of 80 v/v % aqueous ethanol solution. After removing ethanol in the eluate, the resulting solution was freeze-dried into a solid product, B-r.

The solid product B-r contained 81% by weight of α-monoglucosyl hesperidin, 18% by weight of β-monoglucosyl hesperetin, and one percent by weight of other ingredients, and gave no detection of hesperidin and hesperetin.

After adding with 100 ml of 99 v/v % methanol, the solid product B-r was dissolved therein by heating at 80° C., and allowing it to stand at ambient temperature caused crystallization. The formed crystal was washed with 99 v/v % methanol and dried into 12 g of a solid product, B-r-c. The solid product thus obtained contained 98% by weight of α-monoglucosyl hesperidin, one percent by weight of β-monoglucosyl hesperetin, and one percent by weight of other ingredients, and gave no detection of hesperidin and hesperetin.

These results are in Tables 1 and 2.

Example 2

To the enzyme-treated hesperidin solution as Solution A in Referential Example 1 were added one gram of "GLUCOZYME", a glucoamylase preparation commercialized by Nagase Biochemicals, Ltd., Kyoto, Japan; two grams of "HESPERIDINASE NO.2", a hesperidinase preparation commercialized by Tanabe Seiyaku Co., Ltd., Tokyo, Japan; and 10 g of "CELLULASE A <AMANO> 3", an enzyme preparation of Amanoseiyaku Co., Ltd., Tokyo, Japan, and the resulting solution was adjusted to pH 4.0 using 4-N sulfuric acid, and enzymatically reacted at 55° C. for 48 hours.

After completion of the enzymatic reaction, the reaction mixture was heated to inactivate the remaining enzyme and filtered to obtain an enzyme-treated hesperidin solution as Solution C.

HPLC analysis of Solution C under the conditions described in Referential Example 1 revealed that most of the α-glucosyl hesperidin in Solution A was converted into α-monoglucosyl hesperidin in Solution C, and most (99% or more) of the intact hesperidin in Solution A was converted into hesperetin in Solution C.

Similarly as done in Example 1, Solution C was treated with 1.5 l of "XAD-7", a porous adsorption resin with intermediate polarity, and freeze-dried into a solid product, C-r. The solid product C-r contained 85% by weight of α-monoglucosyl hesperidin, 2% by weight of β-monoglucosyl hesperetin, 12% by weight of hesperetin, and one percent by weight of other ingredients, and gave no detection of hesperidin.

The solid product C-r was mixed with and dissolved by heating at 80° C. in 200 ml of 99 v/v % methanol, and allowing it to stand at ambient temperature caused crystallization. The formed crystal was washed with 99 v/v % methanol and dried into eight grams of a solid product, C-r-c.

The solid product thus obtained contained 96% by weight of α-monoglucosyl hesperidin, two percent by weight of β-monbglucosyl hesperetin, one percent by weight of hesperetin, and one percent by weight of other ingredients, and gave no detection of hesperidin.

These results are in Tables 1 and 2.

Comparative Example 1

To the enzyme-treated hesperidin solution as Solution A in Referential Example 1 was added 1.0 gram of "GLUCOZYME", a glucoamylase preparation commercialized by Nagase Biochemicals, Ltd., Kyoto, Japan, the resulting solution was adjusted to pH 4.0 using 4-N sulfuric acid, and enzymatically reacted at 55° C. for 48 hours.

After completion of the enzymatic reaction, the reaction mixture was heated to inactivate the remaining enzyme and filtered to obtain an enzyme-treated hesperidin solution as Solution D.

HPLC analysis of Solution D under the conditions described in Referential Example 1 revealed that most of the α-glucosyl hesperidin present in Solution A was converted into α-monoglucosyl hesperidin in Solution D, and the intact hesperidin in Solution A was unchanged in Solution D.

Similarly as done in Examples 1 and 2, Solution D was treated with 1.5 l of "XAD-7", a porous adsorption resin with intermediate polarity, and freeze-dried into a solid product, D-r.

The solid product D-r contained 76% by weight of α-monoglucosyl hesperidin, 23% by weight of hesperidin, and one percent by weight of other ingredients, and gave no detection of β-monoglucosyl hesperetin and hesperetin.

Similarly as in Examples 1 an 2, the solid product D-r was mixed with and heated at 80° C. in 100 ml of 99 v/v % methanol, resulting in a dissolution of only a small portion of the solid product D-r. Thus it was substantially difficult to crystallize the contents before collection. The above mixture was further mixed with 100 ml of 99 v/v % methanol and heated at 80° C., resulting in a dissolution of a small portion of the solid product D-r. Thus it was substantially difficult to crystallize α-monoglucosyl hesperidin before collection.

The results are in Tables 1 and 2.

TABLE 1

Weight percentage (% by weight) of ingredients in enzyme-treated hesperidin

| Enzyme treated hesperidin | Ingredient | | | | |
|---|---|---|---|---|---|
| | α-Mono-glucosyl hesperidin | Hesperidin | β-Mono-glucosyl hesperetin | Hesperetin | Other ingredients |
| B-r | 81 | 0 | 18 | 0 | 1 |
| C-r | 85 | 0 | 2 | 12 | 1 |
| D-r | 76 | 23 | 0 | 0 | 1 |

TABLE 2

Weight percentage (% by weight) of crystals

| Enzyme treated hesperidin | Ingredient | | | | |
|---|---|---|---|---|---|
| | α-Mono-glucosyl hesperidin | Hesper-idin | β-Mono-glucosyl hesperetin | Hesper-etin | Other ingredients |
| Example 1 (B-r-c) | 98 | 0 | 1 | 0 | 1 |
| Example 2 (C-r-c) | 96 | 0 | 2 | 1 | 1 |
| Comp. Ex. 1 (uncrystal-izable) | — | — | — | — | — |

We claim:

1. A process for producing a high α-monoglucosyl hesperidin content product, comprising:

contacting glucoamylase and α-L-rhamnosidase with a solution containing α-glucosyl hesperidin and hesperidin simultaneously or successively to obtain a mixture;

crystallizing and separating α-monglucosyl hesperidin in and from the mixture; and collecting the high α-monoglucosyl hesperidin content product.

2. A process for producing a high α-monoglucosyl, hesperidin content product, comprising:

contacting glucoamylase, α-L-rhamnosidase, and β-D-glucosidase with a solution containing α-glucosyl hesperidin and hesperidin simultaneously or successively to obtain a mixture;

crystallizing and separating α-monglucosyl hesperidin in and from the mixture; and collecting the high α-monoglucosyl hesperidin content product.

3. The process as claimed in claim 1, further comprising:

crystallizing said α-monoglucosyl hesperidin in a lower alcohol to separate said high α-monoglucosyl content product; and collecting the separated product.

4. The process as claimed in claim 1, wherein said high α-monoglucosyl hesperidin content product contains at least 85% by weight of α-monoglucosyl hesperidin.

5. The process as claimed in claim 2, further comprising:

crystallizing said α-monoglucosyl hesperidin in a lower alcohol to separate said high α-monoglucosyl content product; and collecting the separated product.

6. The process as claimed in claim 2, wherein said high α-monoglucosyl hesperidin content product contains at least 85% by weight of α-monoglucosyl hesperidin.

7. The process as claimed in claim 3, wherein said high α-monoglucosyl hesperidin content product contains at least 85% by weight of α-monoglucosyl hesperidin.

8. The process as claimed in claim 5, wherein said high α-monoglucosyl hesperidin content product contains at least 85% by weight of α-monoglucosyl hesperidin.

* * * * *

UNITED STATES PATENT AND TRADEMARK OFFICE
CERTIFICATE OF CORRECTION

PATENT NO. : 6,048,712
DATED : April 11, 2000
INVENTOR(S) : Toshio Miyake et al.

It is certified that error appears in the above-identified patent and that said Letters Patent is hereby corrected as shown below:

Title page,
Item [73] Assignee: after "Hayashibara" delete semicolon (one assignee).

Column 4
Line 12 before "α" delete left parenthesis "(".
Line 29 "a-monoglucosyl" should read --α-monoglucosyl--.

Column 6
Line 55 "and is to provides" should read --and provides--.

Column 7
Line 46 "Solution Contianing" should read --Solution Containing--.
Line 46 "α-Glucsyl" should read --α-Glucosyl--.

Column 8
Line 35 before "0.01" delete "5".

Column 9
Line 11 "a-glucosyl" should read --α-glucosyl--.

Column 12
Line 25 "e.g., 250°C" should read --e.g., 25°C--.
Line 55 "products image" should read --products' image--.

Column 15
Line 23 "RESPERIDINASE" should read --HESPERIDINASE--.

UNITED STATES PATENT AND TRADEMARK OFFICE
CERTIFICATE OF CORRECTION

PATENT NO.    : 6,048,712
DATED         : April 11, 2000
INVENTOR(S)   : Toshio Miyake et al.

It is certified that error appears in the above-identified patent and that said Letters Patent is hereby corrected as shown below:

Column 16
Line 40 "β-monbglucosyl" should read --β-monoglucosyl--.

Column 18
Line 14, Claim 2, after "high α-monoglucosyl" delete comma (,).

Signed and Sealed this

Nineteenth Day of June, 2001

*Attest:*

Nicholas P. Godici

*Attesting Officer*

NICHOLAS P. GODICI
*Acting Director of the United States Patent and Trademark Office*